United States Patent [19]
Turner et al.

[11] Patent Number: 5,824,680
[45] Date of Patent: Oct. 20, 1998

[54] IPSAPIRONE FOR THE TREATMENT OF ALZHEIMER'S DISEASE BY IMPROVING MEMORY

[75] Inventors: Jonathan Turner; Belinda Cole, both of Berlin, Germany

[73] Assignee: Bayer Aktiengesellschaft, Leverkusen, Germany

[21] Appl. No.: 464,947

[22] Filed: Jun. 5, 1995

Related U.S. Application Data

[63] Continuation of Ser. No. 39,128, Apr. 15, 1993, abandoned.

[30] Foreign Application Priority Data

Aug. 31, 1991 [DE] Germany .......................... 41 35 551.2

[51] Int. Cl.⁶ .......................... A61K 31/495; A61K 31/50
[52] U.S. Cl. .......................... 514/253; 514/252
[58] Field of Search ...................... 514/253, 252

[56] References Cited

U.S. PATENT DOCUMENTS

| | | | |
|---|---|---|---|
| 4,423,049 | 12/1983 | Temple Jr. ............... | 424/251 |
| 4,438,119 | 3/1984 | Allen et al. . | |
| 4,687,772 | 8/1987 | Alderdice ............... | 514/273 |
| 5,013,761 | 5/1991 | Beedle et al. ............ | 514/650 |
| 5,096,908 | 3/1992 | Gidda et al. ............. | 514/307 |

FOREIGN PATENT DOCUMENTS

| | | |
|---|---|---|
| 0 041 488 | 12/1981 | European Pat. Off. . |
| 0 345 948 | 12/1989 | European Pat. Off. . |
| 0 390 424 | 10/1990 | European Pat. Off. . |
| 4 039 631 | 6/1992 | Germany . |
| 1 567 845 | 5/1980 | United Kingdom . |
| 2 222 768 | 3/1990 | United Kingdom . |

OTHER PUBLICATIONS

Dialog Information Services, File 73, Embase, Dialog accession No. 8029555, Embase accession No. 91057805, Murphy D.L.: "Neuropsychiatric disorders and the multiple brain serotonin receptor subtypes and subsystems", *Neuropsychopharmacology* (USA), 3/5–6:457–471, 1990.

Merck Manual, pp. 1305–1309, 1402, 1982.

Przegalinski, Medline Abstract 90349042 of *Neuropharmacology*, 29(6): 521–6, 1990.

Elliott et al., Medline Abstract 9107332 of *Neuropharmacology*, 29(10): 949–56, 1990.

Dialog Information Services, File 155, Medline, Dialog accession No. 07610664, Medline accession No. 9112–664, Rydelek–Fitzgerald et al., "NAN–190: Agonist and Antagonist Interactions with Brain 5–HT1A Receptors", *Brain Res.*, 532(1–2):191–196, 1990.

Tiller et al., *The Lancet*, No. 8609, p. 510, 1988.

Colenda, *The Lancet*, No. 8595, p. 1169, 1988.

Chopin et al., *Psychopharmacology*, 106–26–30, 1992.

Murray et al., *Psychopharmacology*, 105:134–136, 1991.

Wenger et al., *T. J. of Pharmacolog and Exper. Therap.*, vol. 254(1):258–269, 1990.

*Primary Examiner*—William R.A. Jarvis
*Attorney, Agent, or Firm*—Sprung Kramer Schaefer & Briscoe

[57] ABSTRACT

The new use of ipsapirone for the treatment of Alzheimer's Disease by improving memory is described.

1 Claim, 3 Drawing Sheets

IPSAPIRONE FOR THE TREATMENT OF ALZHEIMER'S DISEASE BY IMPROVING MEMORY

This is a continuation of the application Ser. No. 08/039,128 filed Apr. 15, 1993, now abandoned. This application claims priority to PCT/DE92/00720, filed Aug. 28, 1992.

The invention relates to a new use for antagonists or partial agonists on the 5-$HT_{1a}$ receptor or their physiologically compatible salts for the production of a pharmaceutical agent for the prevention and treatment of cognitive disorders, pharmaceutical agents against cognitive disorders that contain this compound as well as the process for the production of this agent.

BACKGROUND OF THE INVENTION

Serotonin (5-hydroxytryptamine, 5-HT) is a neurotransmitter that is released by specific neuronal cell groups, that are in the mid brain and that innervate the entire brain. The aminergic neurotransmitter serotonin released from the neurons has modulating effects on target structures, and the effects are imparted by pharmacologically different receptors. These receptors are classified as follows: 5-$HT_1$-like with subtypes a-e, 5-$HT_2$, 5-$HT_3$ and 5-$HT_4$ receptors. Of the known 5-$HT_1$ receptors, so far the 5$HT_{1a}$ subtype was tested most, since a selective agonist is available with 8-hydroxydipropylamino-tetralin (8-OH-DPAT).

It is known from EP-A-0041488 that 5$HT_{1a}$ agonists can be used in diseases that are based on a serotinin deficiency, such as senility disorders of the mental function, for example, senile dementia. Further, it is described in EP-A-0345 948 that 5$HT_{1a}$ agonists such as 8-OH-DPAT are suitable for the treatment of cerebral ischemia after cardiac arrest or stroke and for the treatment of multiinfarct dementia.

By 5-$HT_{1a}$ agonists is meant compounds that bind to the 5-$HT_{1a}$ receptor and trigger the biological response. By 5-$HT_{1a}$ antagonists is meant compounds that bind to the 5-$HT_{1a}$ receptor and block the biological response. By 5-$HT_{1a}$ partial agonists is meant compounds that directly activate the 5-$HT_{1a}$ receptor but trigger a weaker max. effect.

Surprisingly it was found that antagonists or partial agonists on 5-$HT_{1a}$ receptors bring about an improvement of the cognitive performance.

Because of their mode of action, antagonists and partial agonists on the 5-$HT_{1a}$ receptor are suitable for the treatment and prevention of cognitive deficiencies that can occur in older humans or in Alzheimer's disease, in Parkinson's disease with associated cognitive impairment, in AIDS-dependent dementia and other cognitive impairments.

SUMMARY OF THE INVENTION

According to the invention partial 5-$HT_{1a}$ receptor agonists are suitable, that have an intrinsic activity less than that of 5-carboxamindotryptamine and 5-$HT_{1a}$ receptor antagonists, i.e., compounds that bind to the 5-$HT_{1a}$ receptor and that counteract the effect caused by agonists.

DETAILED DESCRIPTION OF THE DRAWINGS

FIG. 1 shows that 1–2 mg/kg Nan 190 administered 30 minutes before the learning phase brings about an improved memory of escape behavior while 4.0 mg/kg of Nan 190 has no effect.

DETAILED DESCRIPTION OF THE INVENTION

Figure 1:
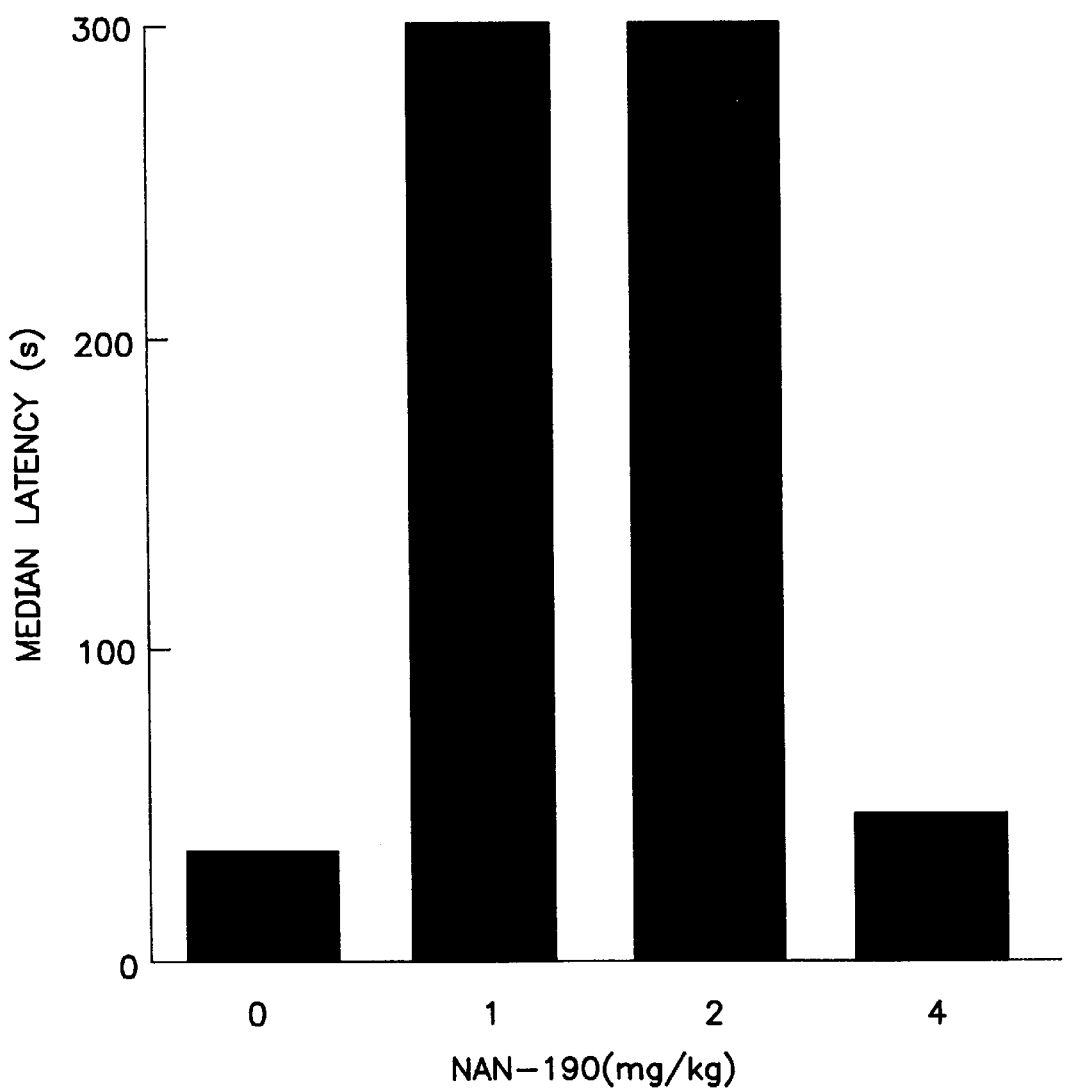

The methods for determining the 5-$HT_{1a}$ antagonistic or agonistic activity are described, for example, in J. Pharmacol. Exp. Ther. 238, 248–253 (1986) and J. Pharmacol. Exp. Ther. 258, 58–65 (1991).

As synthetic chemical compounds that show the effect according to the invention there can be mentioned, for example, the following classes of partial 5-$HT_{1a}$ receptor agonists and 5$HT_{1a}$ receptor antagonists:

1) Piperazine derivatives such as 1,2-methoxyphenyl-4-[4(2-phthalamidebutyl]-piperazine-hydrochloride (NAN-190), e.g., Rydelek-Fitzgerald et al., Brain Res. 532 191–196, 1990); 2-[4[4-(2-pyrimidinyl)-1-piperazinyl] butyl]-1,2-benzisothiozolin-3-on-1,1-dioxide (ipsapirone) (e.g. O'Connor et al., Brit. J. Pharmacol. 101 171–177, 1990); N-[4-[4-(2-pyridinyl)-1-piperazinyl]butyl]-1,1-cyclopentanediacetamide (buspirone) (e.g., deVivo and Maayani, J. Pharmacol. Exp. Ther. 238 248–253, 1986); 8-[2-[4-(2-methoxyphenyl)-1-piperazinyl)ethyl]-8-azaspiro [4,5]decane-7,9-dione (BMY 7378, e.g. Yocca et al., Eur. J. Pharmacol. 137 293–294, 1987); 3,3-dimethyl-1-[4-[4-(2-pyrimidinyl)-1-piperazinyl]butyl]glutarimide) (gepiron) (e.g. Eison et al., Pharmacol. Biochem. Behav. 24 701 1986) 1-[10,11-dihydro-8(methylthio)-dibenzo[b,f]thiepin-10-yl]-4-methylpiperazine (methiothepin).

2) Benzodioxanes such as 8-(4-[(1,4-benzodioxan-2ylmethyl)amino]butyl]-8-azaspiro[4,5]decane-7,9-dione (MDL 72832 e.g., Hibert et al., J. Med. Chem. 31 1087–1093, 1988; 8[2-[(2,3dihydro-1,4-benzodioxin-2-yl) methylamino]ethyl]-8-azaspiro[4,5]decane-7,9-dione (MDL 73005 EF, e.g., Hibert, M. et al., Brit, J. Pharmacol. 93 Suppl. 2P, 1988; Moser, P. et al. ibid 3P).

3) 1,1-Diethyl-3-(8α-ergolinyl)-urea derivatives such as lisuride (e.g., the Vivi and Maayani, J. Pharmacol. Exp. Ther. 238 248–253) and terguride (e.g., Kehr, Eur. J. Pharmacol. 97, 111–119, 1984).

4) 2-Amino-tetralins such as 5-fluoro-8-hydroxy-2 (dipropylamino)-tetralin (J. Med. Chem. 1990, 33, 1541–1544) and spiperone (8-[3-(p-fluorobenzoyl)propyl]-1-phenyl-1,3,8triazaspiro[4,5]decan-4-one).

The physiologically compatible acid addition salts of the above active ingredients as well as all possible isomers (stereoisomers and/or enantiomers) and their mixtures can be used according to the invention.

The physiologically compatible salts are derived from alkaline metals or alkaline-earth metals or the usual inorganic or organic acids such as hydrochloric acid, hydrobromic acid, sulfuric acid, phosphoric acid, citric acid, maleic acid or fumaric acid. The actions according to the invention are shown by the example of 1,2-methoxyphenyl-4-[4-(2-phthalamide)butyl]piperazinehydrochloride (NAN-190) and ipsapirone:

1. Method: "Single trial passive avoidance" in rats

In this test the ability of rats to remember a learned behavior after 48 hours is measured. It is interpreted as a measurement of long-term memory.

On the first day of the learning the animals are placed on a platform. When they jump down, they receive a short foot shock and are then immediately taken from the device. Two days later the animals are again placed on the same platform and the time that they remained on the platform before jumping down is measured (up to a maximum of 300 sec). The prolonged time before jumping down reflects the ability to remember the punishment experience of the first day. The test substance was administered 30 minutes before the learning phase to increase the assurance that the substance-imparted effect is attributable to the improved learning. NAN-190 is a mixed agonist/antagonist in different in vivo and in vitro test processes. 10 animals per group were administered 1.0; 2.0 or 4.0 mg/kg of NAN-190, dissolved in 0.85% of NaCl, i.p. Only vehicle was administered in a control group of 10 animals.

The results show that NAN-190 (1.0 and 2.0 mg/kg i.p., administered 30 minutes before the learning phase) bring about an improved memory of the escape behavior, while 4.0 mg/kg of NAN190 has no effect (FIG. 1). In the learning phase, the treated animals show no differences in comparison with the control animals in the delay of jumping down from the platform, an indication that the treatment has not brought about any non-specific effects on performance variables.

The data was statistically analyzed by nonparametric information statistics. The number of animals that jumped down from the platform as compared with the number of animals that remained on the platform for 300 sec. (e.g., that showed perfect behavior adherence) was used as a variable. This analysis showed an overall effect of the drug treatment (21=46, 78; df=23;p<0.001), since more animals showed a perfect behavior adherence after treatment with 1.0 or 2.0 mg/kg of NAN-190 than after vehicle treatment. No recognizable difference resulted between the control animals and the groups treated with 4.0 mg/kg of NAN-190. The results show that the treatment with NAN-190 of 1.0 mg/kg and 2.0 mg/kg brought about an improved learning.

2. Method: Delayed non-matching to position in rats

In this test the ability of rats is measured to remember a spatial arrangement. The test is interpreted as a measurement of short-term memory.

For this purpose, rats were trained in a standardized so-called "operant chambers" to remember the spatial arrangement (right or left lever of the chamber) of their last response and to react accordingly. Correct responses (matches) were rewarded by being given something to eat. The worsening of the memory caused by time can be tested by varying the time interval between presentation of the test (right or left lever). Test substances that had no specific effect on the memory influence the accuracy of the responses independently of the delay, while test substances that especially influence the working short-term memory, bring about a worsening or improvement of the performance that is directly dependent on the time delay.

In the first experiment ipsapirone HCl, dissolved in 0.85% NaCl, was injected 30 min before the beginning of the test (i.p., n=12 rats). All rats were tested with all dosages (0, 1, 3 and 10 mg/kg), the dosages were administered corresponding to a "Latin Square design". At least 2 test runs were performed without administration of test substance for separation of the test substance tests. In the second experiment the ability of ipsapirone HCl to offset an adverse effect caused by scopolamine was examined. For this purpose rats (n=12) were administered scopolamine HCl (0.14 mg/kg, dissolved in 0.85% NaCl) i.p. 45 minutes before beginning the test, followed by a 15-minute delayed administration of ipsapirone HCl (dosage and experimental performance see above).

Figure 2:
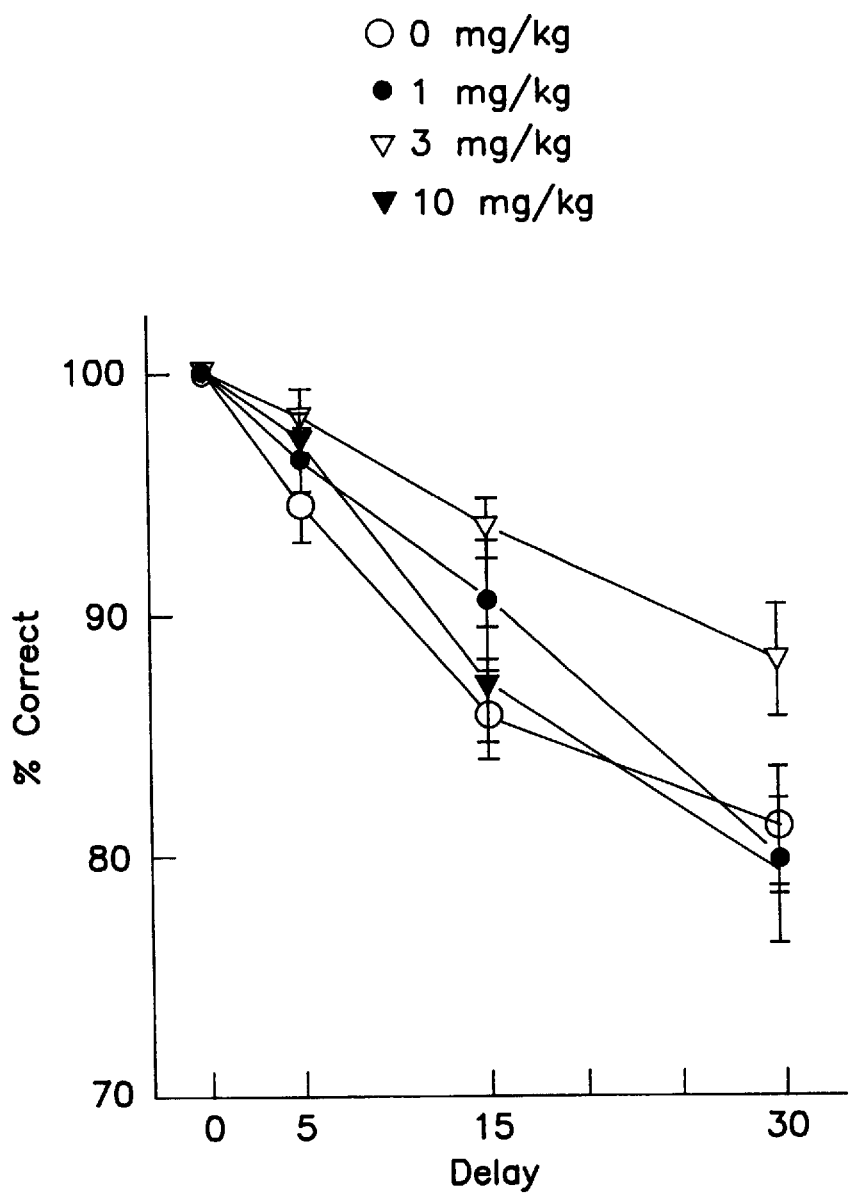
FIG. 2 shows that ipsapirone when administered alone improves the performance in the "delayed matching".
Figure 3:
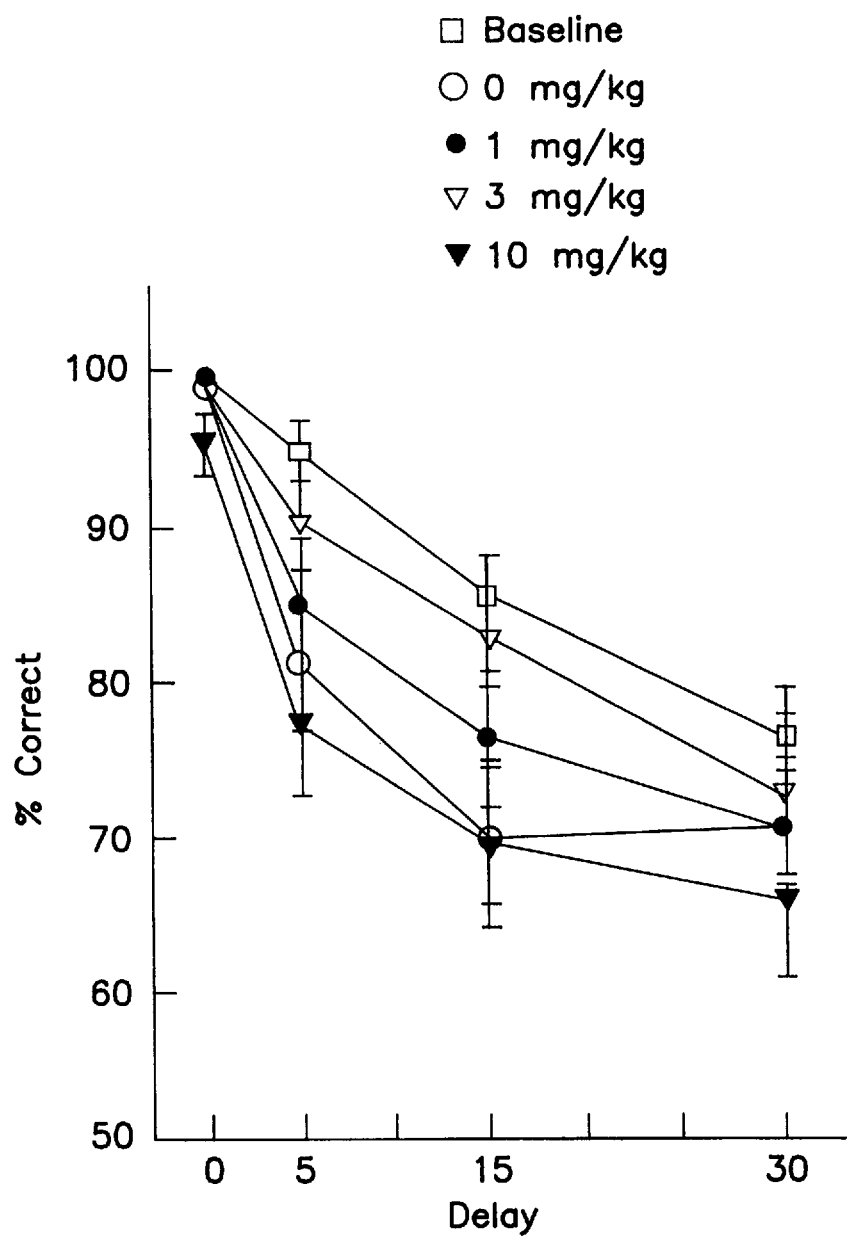
FIG. 3 shows the effect of ipsapirone in countering the adverse effect of scopolamine on the accuracy of the delayed matching responses.

The results of these experiments show that ipsapirone, when it is administered by itself, improves the performance in the "delayed matching" (see description) (see FIG. 2). This is especially noticeable in the longer time intervals (15 and 30 sec.). Scopolamine administration causes a drastic adverse effect on the accuracy of the responses, that is directly connected with the delay. This effect is completely counteracted by the administration of ipsapirone (3.0 mg/kg) (see FIG. 3).

The data was statistically analyzed by a factorial variance analysis with the factor "delay time" and dose. In the second experiment the analysis showed a significant effect relative to the time delay since the accuracy of the correct responses decreased with time (F=104.02, df=3.33, p<0.001) and a significant effect in the dosage (F=3.96, df=3.33, p<0.001). A post hoc analysis according to Newman Keul showed that the rats provided significantly more frequent correct responses, if they were pretreated with 3 mg/kg of ipsapirone. In the third experiment the statistical analysis also showed a significant effect relative to the time delay, since the frequency of the correct responses decreased with time (F=55.647, df=3.33, p<0.001), a significant effect in the dosage (F=4.91, df=4.44, p<0.005) and a significant dosage: time interaction (F=2.19, df=12.132, p=0.01). A post hoc analysis showed that scopolamine has a significant adverse effect on the accuracy of responses in comparison with the control level. If the scopolamine administration was followed by an administration of ipsapirone (3 mg/kg) the test results relative to the accuracy of the responses were not significantly different from the control tests, i.e., the effect of scopolamine was completely canceled out.

These results show that ipsapirone improves the short-term memory and further can counteract the cognition-disturbing effects of scopolamine (a common, pharmacological model of the cognitive losses in the SDAT).

Based on the test results the above-described compounds bring about an improvement of cognitive functions both preventively and therapeutically analogously to hydergine and piracetam.

The invention also comprises pharmaceutical agents that contain the above-mentioned compounds in an effective amount, their production and use for the treatment and prevention of the above-mentioned diseases. The pharmaceutical agents are produced according to processes known in the art, by the active ingredient being brought into the form of a pharmaceutical preparation, with suitable vehicle, auxiliary and/or addition substances, that is suitable for enteral or parenteral administration. The administration can take place orally or sublingually, as a solid in the form of capsules or tablets or as liquid in the form of solutions, suspensions, elixirs or emulsions or rectally in the form of suppositories or the form of injection solutions optionally also usable subcutaneously. As auxiliary agents for the desired pharmaceutical agent formulation the inert organic and inorganic vehicles known to one skilled in the art are suitable such as, for example, water, gelatin, gum arabic, lactose, starch, magnesium stearate, talc, vegetable oils, polyalkylene glycols, etc. Optionally, moreover, they can contain preservatives, stabilizers, wetting agents, emulsifiers or salts to change the osmotic pressure or buffers.

The pharmaceutical preparations can be available in solid form, for example, as tablets, coated tablets, suppositories, capsules, or in liquid form, for example, as solutions, suspensions or emulsions or can be formulated as depot preparations.

As vehicle system interface-near auxiliary agents such as salts of bile acids or animal or vegetable phospholides, but also mixtures of them as well as liposomes or their components, can be used.

For oral use, tablets, coated tablets or capsules with talc and/or hydrocarbon vehicles or binders, such as, for example, lactose, corn or potato starch, are especially suitable. The use can also take place in liquid form, such as, for example, as juice, to which a sweetener is optionally added.

The dosage of the active ingredients can vary according to method of administration, age and weight of the patient, type and severity of the disease to be treated and similiar factors. The daily dose is 0.2–200 mg, and the dose can be given as a single dose administered all at once or subdivided into 2 or more daily doses. Generally the active ingredient is administered one to four times a day, optionally also together with other therapeutic active ingredients. The pharmaceutical agents according to the invention generally contain 0.01 to 20% by weight of active ingredient relative to the preparation.

We claim:

1. A method of treating Alzheimer's Disease in a patient suffering therefrom by improving the memory of said patient, said method comprising administering to said patient a memory improving effective amount of ipsapirone or a physiologically compatible salt thereof.

* * * * *